(12) United States Patent  
Tarui

(10) Patent No.: US 7,230,260 B1  
(45) Date of Patent: Jun. 12, 2007

(54) RAINDROP SENSOR

(75) Inventor: Jun Tarui, Kariya (JP)

(73) Assignee: DENSO Corporation, Kariya, Aichi-pref. (JP)

( * ) Notice: Subject to any disclaimer, the term of this patent is extended or adjusted under 35 U.S.C. 154(b) by 0 days.

(21) Appl. No.: 11/600,889

(22) Filed: Nov. 17, 2006

(30) Foreign Application Priority Data

Nov. 21, 2005 (JP) .............................. 2005-336128

(51) Int. Cl.
G01N 21/49 (2006.01)
H01J 5/16 (2006.01)

(52) U.S. Cl. .................................. 250/574; 250/227.25

(58) Field of Classification Search ........ 250/573–575, 250/227.25; 356/445; 73/170.17, 170.21; 340/602–604; 318/483
See application file for complete search history.

(56) References Cited

U.S. PATENT DOCUMENTS

| | | | |
|---|---|---|---|
| 4,588,935 A * | 5/1986 | Kaneiwa et al. ............. | 318/483 |
| 4,701,613 A * | 10/1987 | Watanabe et al. ........... | 340/602 |
| 5,661,303 A * | 8/1997 | Teder ...................... | 250/227.25 |
| 5,861,758 A * | 1/1999 | Berberich ................... | 324/694 |
| 5,898,183 A | 4/1999 | Teder | |
| 6,331,819 B1 * | 12/2001 | Hog .......................... | 340/604 |
| 6,507,015 B1 | 1/2003 | Maeno et al. | |
| 6,686,603 B2 * | 2/2004 | Ishikawa .................... | 250/573 |
| 6,765,631 B2 | 7/2004 | Ishikawa et al. | |
| 2006/0076524 A1 * | 4/2006 | Yoshigoe et al. ............ | 250/573 |
| 2007/0034785 A1 * | 2/2007 | Yoshigoe et al. ........ | 250/227.25 |

* cited by examiner

*Primary Examiner*—John R. Lee
(74) *Attorney, Agent, or Firm*—Nixon & Vanderhye P.C.

(57) ABSTRACT

A raindrop sensor for sensing water attached to a second surface of a transparent body includes a light emitting element, a light guide body, a light receiving element, and an abnormality determining device. The light emitting element is provided in a first surface side of the transparent body for emitting light toward the transparent body. The light guide body is mounted on a first surface of the transparent body for guiding the light. The light receiving element is provided in first surface side of the transparent body for receiving the reflected light, which is reflected by the second surface of the transparent body. The light receiving element outputs a signal based on an amount of the reflected light received. The abnormality determining device determines an abnormality of the light guide body by comparing a value indicated by the signal with an index value.

8 Claims, 3 Drawing Sheets

RAINDROP SENSOR

CROSS REFERENCE TO RELATED APPLICATION

This application is based on and incorporates herein by reference Japanese Patent Application No. 2005-336128 filed on Nov. 21, 2005.

BACKGROUND OF THE INVENTION

1. Field of the Invention

The present invention relates to a raindrop sensor, and more particularly to a raindrop sensor, which is preferably applied to, for example, a wiper controller for a vehicle.

2. Description of Related Art

Japanese Unexamined Patent Publication No. 2001-66246 corresponding to U.S. Pat. No. 6,507,015 discloses a raindrop sensor, which is mounted on an inner surface of a windshield and senses raindrops attached to an outer surface of the windshield. The raindrop sensor includes a light emitting element, a light guide body, and a light receiving element. The light emitting element emits light in a direction from the inner surface to the outer surface. The light guide body guides the light to the outer surface, and also guides a reflected light, which is reflected by the outer surface, toward the inner surface side. The light receiving element receives the light from the light guide body, and generates a signal according to an amount of the received light. The raindrop sensor compares an amount of the light received in a clear whether condition with a current amount of the light currently received in order to determine whether moisture, such as raindrops, is attached to the outer surface or not.

Also, Japanese Unexamined Patent Publication No. 2001-521158T corresponding to U.S. Pat. No. 5,898,183 discloses a raindrop sensor, which includes a light guide body having a prism body and a flexible interlayer. In the raindrop sensor, a silicone sheet, for example, serves as the interlayer, which is held between the windshield and the prism body. Thus, this limits an air layer from forming between the prism body and the windshield such that the light, which travels through the prism body, can be guided to the outer surface of the windshield.

However, in assembly of the raindrop sensor to the inner surface, when the prism body is attached to the inner surface directly without the interlayer, the air layer is formed between the prism body and the inner surface. Then, the light, which travels through the prism body, may not reach the windshield, but may reflects off the end face of the prism body. Thus, the raindrop may not be detected because the light emitted by the light emitting element does not sufficiently reach the outer surface of the windshield.

To deal with the above disadvantages, in a factory for attaching the raindrop sensor, an operator checks whether the silicone sheet, which is a part of the light guide body, is appropriately attached or not by visual examination. However, because this silicone sheet is provided at the back of the raindrop sensor and thus the silicone sheet is behind a cover thereof, it is often difficult for the operator to check by the visual examination.

SUMMARY OF THE INVENTION

The present invention is made in view of the above disadvantages. Thus, it is an objective of the present invention to address at least one of the above disadvantages.

To achieve the objective of the present invention, there is provided a raindrop sensor, which is provided in a first surface side of a transparent body for sensing water attached to a second surface of the transparent body, the raindrop sensor including a light emitting element, a light guide body, a light receiving element, and an abnormality determining device. The light emitting element is provided in the first surface side of the transparent body for emitting light toward the transparent body. The light guide body is mounted on a first surface of the transparent body. The light guide body guides the light, which is emitted by the light emitting element, to the transparent body. The light guide body guides the light, which is reflected by the transparent body, to the first surface side of the transparent body. The light receiving element is provided in the first surface side of the transparent body for receiving the reflected light, which is reflected by the second surface of the transparent body, and the light receiving element outputs a signal based on an amount of the reflected light received by the light receiving element. The abnormality determining device determines an abnormality of the light guide body by comparing a value indicated by the signal outputted by the light receiving element with an index value.

BRIEF DESCRIPTION OF THE DRAWINGS

The invention, together with additional objectives, features and advantages thereof, will be best understood from the following description, the appended claims and the accompanying drawings in which:

DETAILED DESCRIPTION OF PREFERRED EMBODIMENTS

First Embodiment

Figure 1:
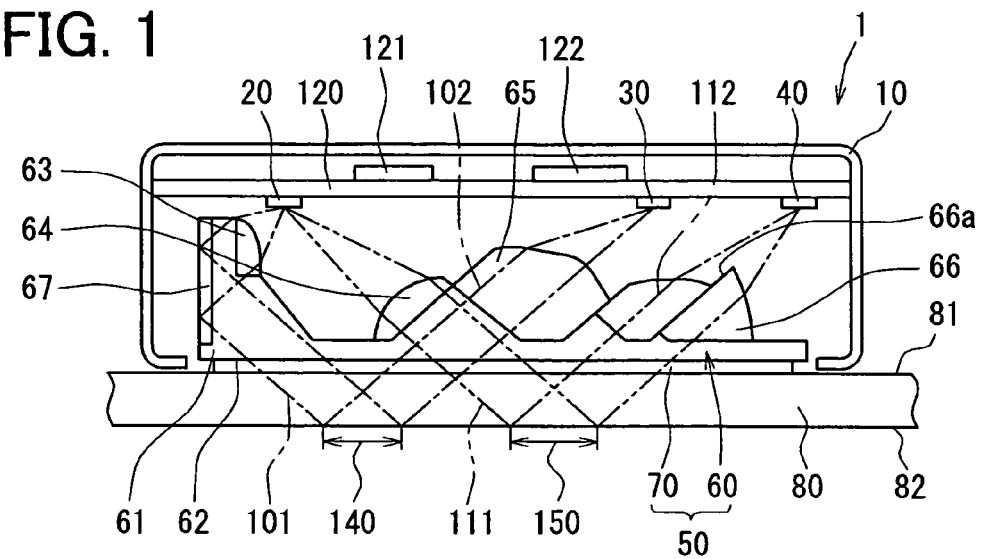
FIG. 1 is a side view of a raindrop sensor according to a first embodiment of the present invention.

The first embodiment of the present invention will be described with reference to accompanying drawings. A raindrop sensor shown in FIG. 1 is, for example, applied to a wiper controller that controls a wiper (not shown) provided to an outer surface of a front windshield (transparent body) 80 of a vehicle. The wiper is controlled by the wiper controller based on a sensing output from a raindrop sensor 1, and slides within a wipe range on an outer surface (second surface) 82 of the windshield 80.

The raindrop sensor 1 is provided from an inner surface 81 side (first surface side) of the windshield 80 according to the wiping range. That is, the raindrop sensor 1 is provided in a space defined adjacent to an inner surface (first surface) 81 of the windshield 80. The raindrop sensor 1 optically senses raindrops, which drop on the wipe range of the windshield 80, to output a signal to the wiper controller.

Figure 2:
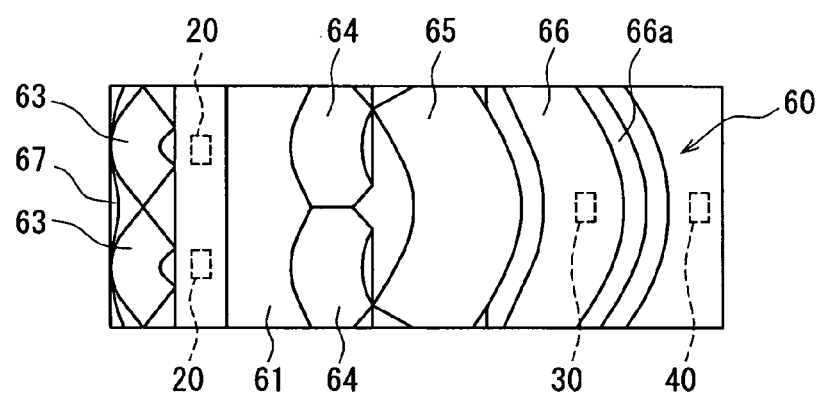
FIG. 2 is a plan view of a prism shown in FIG. 1.

FIG. 1 is a side view of the raindrop sensor 1 of the present embodiment. FIG. 2 is a plan view of the raindrop sensor 1 shown in FIG. 1 viewed from above a light guide body 50 of the raindrop sensor 1. FIG. 1 is a side view of raindrop sensor 1 shown in FIG. 2. As shown in FIG. 1, the raindrop sensor 1 includes the light guide body 1, light emitting elements 20, a first light receiving element 30, a second light receiving element 40, a computing element 121, a storing element 122, a circuit substrate 120, and a cover 10. Here, the light guide body 50 includes a prism 60 and a silicone sheet 70.

The prism 60 is made of a transparent resin, and is provided on the inner surface 81 of the windshield 80 through the silicone sheet 70. The prism 60 guides light emitted by the light emitting elements 20 to the windshield 80. Then, the light reflected by the outer surface 82 of the windshield 80 is guided by the prism 60 to the first and second light receiving element 30, 40. A structure of the prism 60 will be described later.

Here, the silicone sheet 70 is of a flexible material, and is provided between the prism 60 and the windshield 80 such that an air layer is limited from forming therebetween. A refraction index of the silicone sheet 70 is nearly equal to that of the windshield 80 such that the light traveling from the prism 60 can be guided to the windshield 80 without deterioration. Also, the light reflected by the outer surface 82 of the windshield 80 can be returned to the prism 60 without deterioration.

Then, the structure of the prism 60 will be detailed with reference to FIGS. 1, 2. The prism 60 has a generally rectangular shape when viewed from above. A longitudinal direction parallel to a long side of the prism 60 is named as a long side direction. A traverse direction parallel to a short side of the prism 60 is named as a short side direction. The prism 60 includes first input side lens portions 63, second input side lens portions 64, a first output side lens portion 65, a second output side lens portion 66, and a body 61.

Each of the first input side lens portions 63 collimates the light emitted by a corresponding one of the light emitting elements 20 such that the collimated light is applied to a predetermined raindrop sensing range 140. Thus, the first input side lens portion 63 is formed relative to the light emitting element 20 such that an optical axis of the first input side lens portion 63 corresponds to a light emitting part of the corresponding light emitting element 20. As shown in FIG. 2, the first input side lens portions 63 are arranged relative to each other in the short side direction at an end portion of the body 61 in the long side direction. The collimated light collimated by each first input side lens portion 63 is named as a first input light 101 (indicated as a chain line in FIG. 1).

Reflecting portions 67 are formed at the end portion of the body 61 to reflect the first input light 101 toward the windshield 80. The reflecting portions 67 are arranged relative to each other in the short side direction similar to the first input side lens portions 63. As shown in FIG. 1, the first input light 101 firstly travels toward an end face of the prism 60, at which the reflecting portions 67 are formed, and then travels toward the windshield 80 after reflected by the corresponding reflecting portion 67.

The second input side lens portions 64 are formed at a position away from the first input side lens portions 63 in the long side direction. Each of the second input side lens portions 64 collimates the light emitted by a corresponding light emitting element 20 such that the collimated light is applied to another predetermined raindrop sensing range 150. Thus, the second input side lens portion 64 is formed relative to the corresponding light emitting element 20 such that a focus of the second input side lens portion 64 corresponds to a light emitting part of the corresponding light emitting element 20. As shown in FIG. 2, the second input side lens portions 63 are arranged relative to each other in the short side direction on the body 61. The collimated light collimated by each second input side lens portion 64 is named as a second input light 111 (indicated as a chain double-dashed line in FIG. 1). The second input light 111 travels toward the windshield 80 generally parallel to the first input light 101 in the long side direction.

Both the first input side lens portion 63 and the second input side lens portion 64 are formed on the body 61 such that an optical axis of each of the lens portions 63, 64 corresponds to the light emitting part of the light emitting element 20. Thus, the light applied from the light emitting element 20 can be diverged into the first input light 101 and the second input light 111. The structures of the first and second input side lens portions 63, 64 correspond to a diverging portion of the present invention. Thus, each light emitting element 20 is associated with the first input light 101 and the second input light 111. As a result, the number of the light emitting elements 20 can be reduced relative to the number of the input lights (the first input light 101 and the second input light 111), and therefore, the raindrop sensor 1 is limited from increasing in size.

As shown in FIG. 1, the first and second input lights 101, 111 reach the raindrop sensing ranges 140, 150, respectively, through the silicone sheet 70 by predetermined input angles. Then, the first and second input lights 101, 111 are reflected by the raindrop sensing range 140, 150 to again travel toward the prism 60. The light reflected by the sensing range 140 is named as a first reflected light 102 (indicated as a chain line in FIG. 1) and the light reflected by the sensing range 150 is named as a second reflected light 112 (indicated as a chain double-dashed line in FIG. 1).

In contrast, the first output side lens portion 65 is formed at a position away from the second input side lens portions 64 in the long side direction toward another end of the body 61 as shown in FIG. 1. The first output side lens portion 65 converges the first reflected light 102 such that the first light receiving element 30 can receive the first reflected light 102.

The second output side lens portion 66 is formed at a position away from the first output side lens portion 65 in the long side direction toward the anther end of the body 61. The second output side lens portion 66 converges the second reflected light 112 such that the second light receiving element 40 can receive the second reflected light 112. A step portion 66a is formed on a generally center of the second output side lens portion 66 on its surface as shown in FIG. 1. A surface shape of the second output side lens portion 66 is not detailed here because a similar lens portion, which is similar to the second output side lens portion 66 of the present embodiment, is disclosed in Japanese Unexamined Patent Publication No. 2001-66246. The prism 60 can be reduced in height because the prism 60 includes a lens shape of the second output side lens portion 66 having the step portion 66a.

A light passage, through which the first input light 101 and the first reflected light 102 travel, corresponds to a first light passage of the present invention. Also, another light passage, through which the second input light 111 and the second reflected light 112 travel, corresponds to a second light passage of the present invention.

The first and second input side lens portions 63, 64, the reflecting portions 67, and the first and second output side lens portions 65, 66 may be integrally formed with the body 61. Also, the above portions 63 to 67 may be separately formed from the body 61 and then, the above portions 63 to 67 may be attached to the surface of the body 61.

The circuit substrate 120, which is fixed to the cover 10, is provided above the prism 60. The light emitting elements 20, the first light receiving element 30, the second light receiving element 40, a computing element 121, and the storing element 122. The computing element 121 receives signals according to amounts of the light received by the first and second light receiving elements 30, 40 to compute amounts of the raindrops attached to the raindrop sensing ranges 140, 150. Also, the computing element 121 receives the above signals to determine the abnormal state of the light guide body 50. The storing element 122 stores index values used when the computing element 121 determines the abnormality of the light guide body 50.

Each of the light emitting element 20 is provided on the circuit substrate 120 such that the light emitting part of the light emitting element 20 corresponds to an intersection of the optical axes of both the first and second input side lens portions 63, 64. Two first input side lens portions 63 are arranged relative to each other in the short side direction. Also, two second input side lens portions 64 are arranged relative to each other in the short side direction. Thus, two light emitting elements 20 are required to correspond to the first and second input side lens portions 63, 64. The light emitting elements 20 are also arranged side by side in the short side direction (see FIG. 2).

The first light receiving element 30 is provided to the circuit substrate 120 such that a light receiving part of the first light receiving element 30 corresponds to a convergent point of the light outputted from the fist output side lens portion 65. The second light receiving element 40 is provided to the circuit substrate 120 such that a light receiving part of the second light receiving element 40 corresponds to a convergent point of the light outputted from the second output side lens portion 66. The second light receiving element 40 is located away from the first light receiving element 30 in the long side direction. In other words, the first and second light receiving elements 30, 40 are provided on the circuit substrate 120 relative to the corresponding light emitting element 20 such that a distance between the first light receiving element 30 and the light emitting element 20 is different from a distance between the second light receiving element 40 and the light emitting element 20. That is, the first light receiving element 30 is provided apart from the light emitting element 20 by a first distance, and the second light receiving element 40 is provided apart from the light emitting element 20 by a second distance, which is different from the first distance.

The computing element 121 is constituted by, for example, a known CPU, and receives signals, which corresponds to the amounts of light received by the first and second light receiving elements 30, 40. Then, the computing element 121 computes the amount of raindrops attached to the raindrop sensing ranges 140, 150. Specifically, the computing element 121 compares the signals received in a non-raindrop state with the current signals currently received to sense the raindrops. Here, in the non-raindrop state, the raindrops are not attached on the raindrop sensing ranges 140, 150.

Also, the computing element 121 determines the abnormal state of the light guide body 50 by comparing the signals with the index values stored in the storing element 122. Determining process for determining the abnormal state will be specifically described later. Here, the storing element 122 includes, for example, a known EEPROM, a known RAM, and a known ROM.

The computing element 121 and the storing element 122 may be provided externally to the raindrop sensor 1 instead of being provided on the circuit substrate 120. Also, the raindrop sensor 1 is not limited to be used for an automobile, but may be used for various vehicles, ships, and air planes.

Next, the determining process for determining the abnormal state of the light guide body 50 will be described with reference to FIGS. 3, 4. FIG. 4 is a flow chart showing a process for determining the abnormal state of the light guide body 50. At step S1, the computing element 121 receives the signals from the first and second light receiving elements 30, 40. Here, each signal corresponds to the amount of the light received by the corresponding light receiving element. At step S2, the computing element 121 computes the amounts of the light received by the first and second light receiving elements 30, 40 based on the above signals inputted at step S1.

Next, the computing element 121 computes a ratio of the light amounts received by the first and second light receiving elements 30, 40. Specifically, the ratio of the light amounts is computed by dividing the amount of the light received by the first light receiving element 30 by the amount of the light received by the second light receiving element 40.

Next, the computing element 121 determines at step S4 to step S8 whether the light guide body 50 is under the abnormal state or not. Before describing the processes shown at and after step S4, the abnormal state of the light guide body 50 will be described with reference to FIG. 3. Here, the abnormal state is, for example, a mounting state of the raindrop sensor 1 on the windshield 80 without the silicone sheet 70 (i.e., the mounting state of the raindrop sensor 1 with the silicone sheet 70 missed). Thus, the light passage in the prism 60 and the light received by the first and second light receiving elements 30, 40 under this mounting state will be described.

Figure 3:
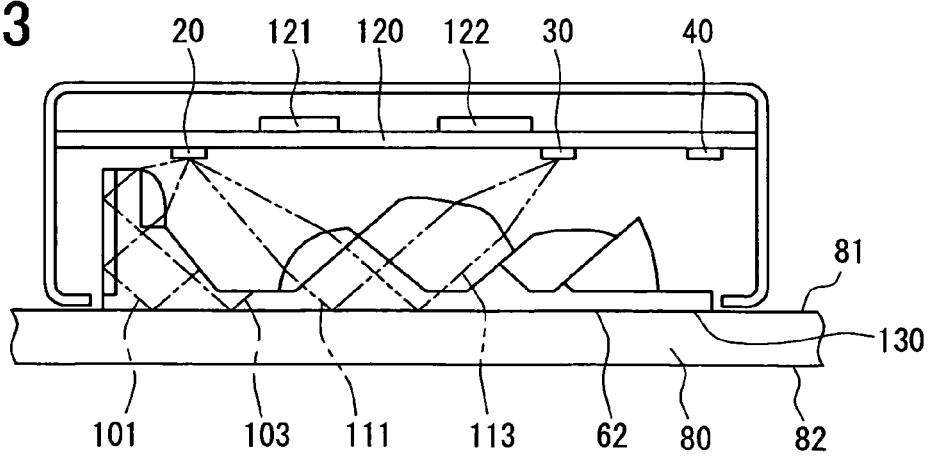
FIG. 3 is a side view of the raindrop sensor, which is mounted on a windshield without a silicone sheet, according to the first embodiment.
Figure 4:
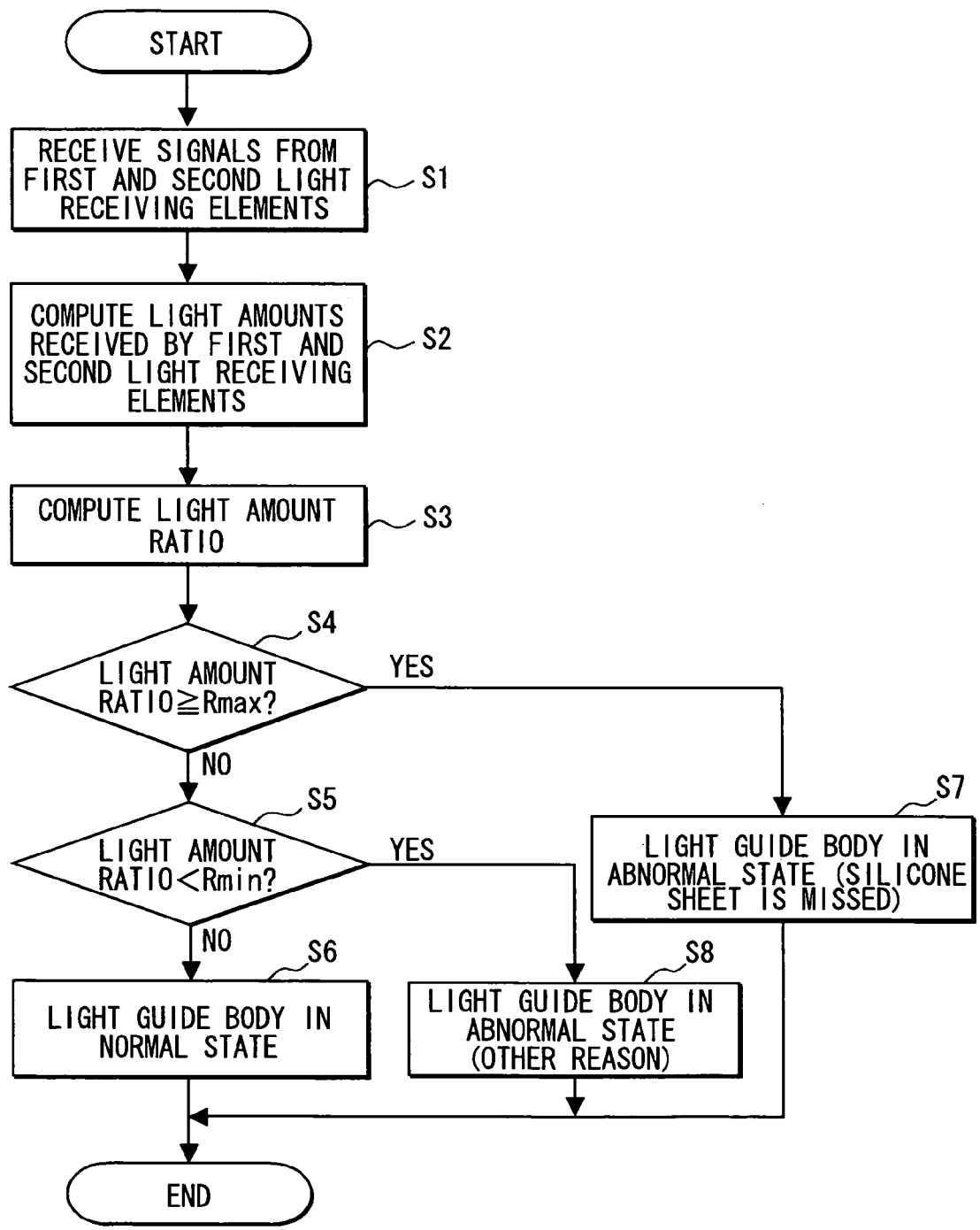
FIG. 4 is a flow chart showing a process for determining an abnormal state of a light guide body of the raindrop sensor according to the first embodiment.

FIG. 3 is the side view of the raindrop sensor 1, which is mounted on the windshield 80 without the silicone sheet 70. The structure of components of the raindrop sensor 1 in FIG. 3 is the same as that in FIG. 1 except that the raindrop sensor 1 in FIG. 3 does not includes the silicone sheet 70. Differences between mounting structure shown in FIG. 1 and that shown in FIG. 3 will be mainly described.

As shown in FIG. 3, the prism 60 directly contacts the inner surface 81 of the windshield 80 without the silicone sheet 70. Thus, the air layer 130 is formed between an end surface 62 of the body 61 of the prism 60 and the inner surface 81 because there is no silicone sheet 70.

When the light is emitted by the light emitting element 20 under this state, the first and second input lights 110, 111 are formed at the first and second input side lens portions 63, 64. These first and second input lights 101, 111, however, cannot reach the outer surface 82 of the windshield 80 but are reflected by the end surface 62 of the body 61 because of the air layer 130. The reflected lights are named as a first abnormal reflected light 103 and a second abnormal reflected light 113.

Because the first and second abnormal reflected lights 103, 113 are reflected at different positions from the first and second reflected lights 102, 112, the passages of the abnormal reflected lights 103, 113 are different from those of the reflected lights 102, 112. As shown in FIG. 3, the first abnormal reflected light 103 does not reach either of the output side lens portions 65, 66, and is outputted through a surface of the body 61. In contrast, the second abnormal reflected light 113 reaches the first output side lens portion 65, and is converged to the first light receiving element 30 as shown in FIG. 3. A light passage, through which the second input light 111 and the second abnormal reflecting light 113 travel, corresponds to a third light passage of the present invention.

Therefore, when the raindrop sensor 1 is mounted without the silicone sheet 70, the light emitted by the light emitting element 20 can be received only by the first light receiving element 30 but not received by the second light receiving element 40. In the present embodiment, each of lens portions 63 to 66 of the prism 60, the reflecting portion 67 are designed, and also the light emitting elements 20, the light receiving elements 30, 40 are positioned such that the first and second light receiving elements 30, 40 can receive the same amount of light when the light guide body 50 is under a normal state (i.e., not the abnormal state). Also, the above portions and elements are designed and positioned such that either one of the first and second light receiving elements 30, 40 can receive the light emitted by the light emitting elements 20 when the light guide body 50 is under the abnormal state (e.g., mounting the raindrop sensor 1 without the silicone sheet 70).

From here, a specific example of the determining process for determining the abnormality of the light guide body 50 will be described. At step S4, the computing element 121 reads Rmax, which is one of the index values stored in the storing element 122, to compare Rmax with the ratio of the light amounts computed at step S3. Rmax is a maximum value of the ratio of the light amounts when the light guide body 50 is under the normal state. When the ratio of the light amounts (light amount ratio) is equal to or larger than Rmax, control continues with step S7, where the computing element 121 stores in the storing element 122 information that the light guide body 50 is mounted on the windshield 80 without the silicone sheet 70. Then, the process ends. When the light amount ratio is less than Rmax, control of the computing element 121 continues with step S5.

At step S5, the computing element 121 reads Rmin, which is another one of the index values stored in the storing element 122, to compare Rmin with the light amount ratio computed at step S3. Rmin is a minimum value of the light amount ratio when the light guide body 50 is under the normal state. When the light amount ratio is equal to or larger than Rmin, control of the computing element 121 continues with step S6, where the computing element 121 stores in the storing element 122 information that the light guide body 50 is not under the abnormal state (i.e., the light guide body 50 is under the normal state). Then, the process ends. When the light amount ratio is less than Rmin, the computing element 121 stores in the storing element 122 information that the light guide body 50 is under the abnormal state by some reasons. The, the process ends. The above step S4 to step S8 corresponds to an abnormality determining device of the present invention.

Then, the state information of the light guide body 50 stored in the storing element 122 is reported to drivers, repair people, and quality control managers in factories through a diagnosis system (not shown).

In the present embodiment, the amount of lights received by the first and second light receiving elements 30, 40 are compared with the index values prestored in the storing element 122 to detect the abnormal state of the light guide body 50. Thus, the visual examination is not employed to detect the abnormal state. Here, the abnormal state is for example the state where the raindrop sensor 1 is mounted without the silicone sheet 70.

Also, in the present embodiment, the ratio of the amounts of light received by the first and second light receiving elements 30, 40 is compared with the index values prestored in the storing element 122 to detect the abnormal state of the light guide body 50. Thus, the abnormal state of the light guide body 50 can be detected independently from the change of light emitting property of the light emitting element 20 according to a change of ambient temperature. Also, the abnormal state can be detected independently from different light transmittances of different windshields 80.

In the present embodiment, the light amount ratio is used to determine the abnormal state. However, a difference between the amount of light received by the first light receiving element 30 and that received by the second light receiving element 40 may be used to determine the abnormal state.

Advantages of using the light amount ratio for detecting the abnormal state of the light guide body 50 will be described in detail. The light emitting property of the light emitting element 20 may change according to the change of the surrounding temperature. Also, the light transmittance of the windshield 80 is different for each different type of the vehicle. When the light emitting property changes, the amount of the light emitted by the light emitting element 20 varies. This results in that the amounts of the light received by the light receiving elements 30, 40 may also vary. Also, when the light transmittance is different, the amounts of the light received by the light receiving elements 30, 40 may also vary.

Therefore, if the index value stored in the storing element 122 were a normal value measured under a certain temperature with the windshield 80 of a certain light transmittance, the abnormal state might not be correctly detected when the temperature changes from the certain temperature or the windshield 80 of the different type is used as described above.

In contrast, in the present embodiment, the abnormal state can be detected without the above disadvantages because the light amount ratio of the first and second light receiving elements 30, 40 is used.

Second Embodiment

Figure 5:
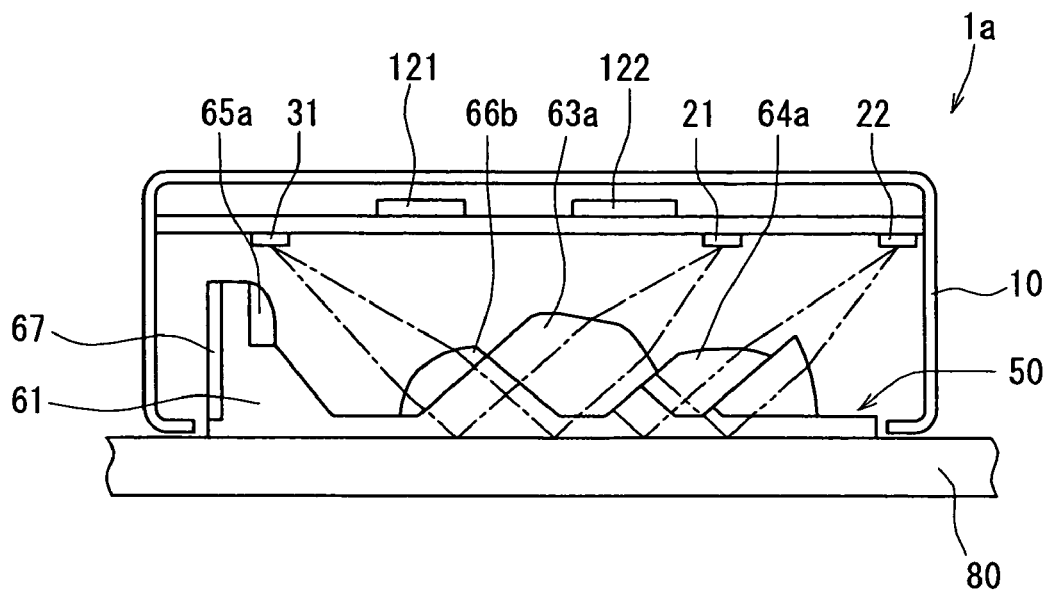
FIG. 5 is a side view of a raindrop sensor, which is mounted on the windshield without the silicone sheet, according to a second embodiment.

Next, the second embodiment of the present invention will be described with reference to FIG. 5. Similar components to those in the first embodiment will be indicated by the same numerals. Characteristic points, which are different from the first embodiment, will be mainly described. FIG. 5 is a side view of a raindrop sensor 1a of the second embodiment. FIG. 5 shows a mounting state of the raindrop sensor 1a on the windshield 80 without the silicone sheet 70 similar to FIG. 3.

Locations of light emitting elements and light receiving elements relative to the light guide body 50 of the raindrop sensor 1a of the present embodiment are changed from the locations of those of the raindrop sensor 1 of the first embodiment shown in FIG. 1 (i.e., locations of the light emitting elements are switched with the locations of the light receiving elements). Specifically, a first light emitting element 21 and a second light emitting element 22 are provided on a right side in FIG. 5. Light receiving elements 31 are provided on a left side in FIG. 5.

Lens portions corresponding to the first and second output side lens portions 65, 66 of the first embodiment are named as first and second input side lens portions 63a, 64a. Lens portions corresponding to the first and second input side lens portions 63, 64 of the first embodiment are named as first and second output side lens portions 65a, 66b.

The first and second output side lens portions 65a, 66b can converge the lights that travel through the body 61. Thus, the first and second output side lens portions 65a, 66b correspond to a converging portion of the present invention. Thus, each light receiving element 31 is associated with the corresponding first and second light emitting element 21, 22. As a result, the number of the light receiving elements 31 can be reduced relative to the number of the light emitting elements, and therefore, the raindrop sensor 1 is limited from increasing in size.

In a structure, where the mounting positions of the light emitting elements are switched with the mounting positions of the light receiving elements, the light receiving elements 31 only receive the light from the first light emitting element 21 if the raindrop sensor 1a is mounted without the silicone sheet 70 as shown in FIG. 5. Thus, the computing element 121 compares the amounts of light received by the light receiving elements 31 with an index value stored in the storing element 122 to determine the abnormal state of the light guide body 50.

Third Embodiment

Figure 6:
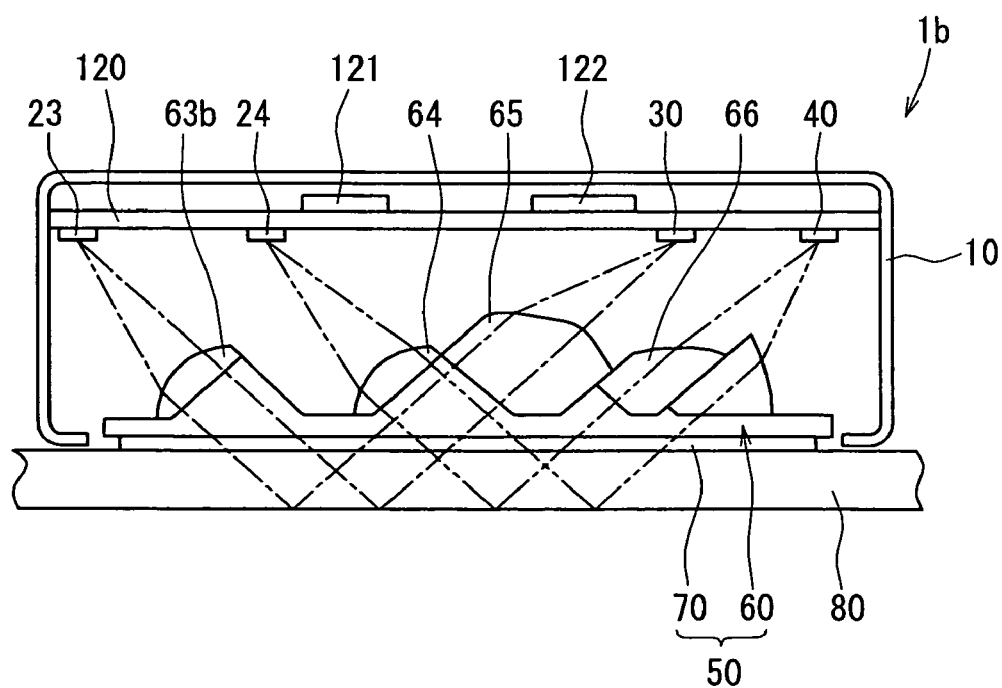
FIG. 6 is a side view of a raindrop sensor according to a third embodiment of the present invention.

Next, the third embodiment of the present invention will be described with reference to FIG. 6. Similar components to those in the first embodiment will be indicated by the same numerals. Characteristic points, which are different from the first embodiment, will be mainly described. FIG. 6 is a side view of a raindrop sensor 1b of the third embodiment.

The raindrop sensor 1b of the present embodiment includes first light emitting elements 23 and second light emitting elements 24. The light emitted by each of the first light emitting elements 23 is inputted into a corresponding one of first input side lens portions 63b, and the light emitted by each of the second light emitting elements 24 is inputted into the corresponding one of the second input side lens portions 64. The above structure is different from the structure of the first embodiment.

Also in the above structure, the amounts of light received by the first and second light receiving elements 30, 40 change due to changes of light passages similar to the first and second embodiment when the raindrop sensor 1b is mounted without the silicone sheet 70. When the process shown in FIG. 4 is executed, the abnormal state of the light guide body 50 can be determined.

Additional advantages and modifications will readily occur to those skilled in the art. The invention in its broader terms is therefore not limited to the specific details, representative apparatus, and illustrative examples shown and described.

What is claimed is:

1. A raindrop sensor, which is provided in a first surface side of a transparent body for sensing water attached to a second surface of the transparent body, the raindrop sensor comprising:
   a light emitting element that is provided in the first surface side of the transparent body for emitting light toward the transparent body;
   a light guide body that is mounted on a first surface of the transparent body, wherein:
      the light guide body guides the light, which is emitted by the light emitting element, to the transparent body; and
      the light guide body guides the light, which is reflected by the transparent body, to the first surface side of the transparent body;
   a light receiving element that is provided in the first surface side of the transparent body for receiving the reflected light, which is reflected by the second surface of the transparent body, the light receiving element outputting a signal based on an amount of the reflected light received by the light receiving element; and
   an abnormality determining device that determines an abnormality of the light guide body by comparing a value indicated by the signal outputted by the light receiving element with an index value.

2. The raindrop sensor according to claim 1, wherein the light receiving element is a first light receiving element that outputs a first signal based on the amount of the reflected light received by the first light receiving element, the raindrop sensor further comprising a second light receiving element that is provided in the first surface side of the transparent body for receiving the reflected light, which is reflected by the second surface of the transparent body, wherein:
   the second light receiving element outputs a second signal based on the amount of the reflected light received by the second light receiving element;
   the light guide body includes:
      a first light passage that guides the light emitted by the light emitting element to the transparent body and guides the reflected light, which is reflected by the transparent body, toward the first light receiving element; and
      a second light passage that guides the light emitted by the light emitting element to the transparent body and guides the reflected light, which is reflected by the transparent body, toward the second light receiving element;
   the abnormality determining device computes one of the followings:
      a ratio of a first value indicated by the first signal to a second value indicated by the second signal; and
      a difference between the first value and the second value; and
   the abnormality determining device determines the abnormality of the light guide body by comparing the computed one of the ratio and the difference with the index value.

3. The raindrop sensor according to claim 2, wherein:
   the first light receiving element is provided apart from the light emitting element by a first distance;
   the second light receiving element is provided apart from the light emitting element by a second distance, which is different from the first distance; and
   the light guide body includes a diverging portion that diverges the light emitted by the light emitting element into a first input light, which travels through the first light passage, and a second input light, which travels through the second light passage.

4. The raindrop sensor according to claim 2, wherein the light emitting element is a first light emitting element that emits the light, which travels through the first light passage, the raindrop sensor further comprising a second light emitting element that is provided in the first surface side of the transparent body for emitting the light, which travels through the second light passage, wherein:
   the first light emitting element is provided apart from one of the first and second light receiving elements by a first distance; and the second light emitting element is provided apart from the one of the first and second light receiving elements by a second distance, which is different from the first distance.

5. The raindrop sensor according to claim 1, wherein the light emitting element is a first light emitting element that emits the light, the raindrop sensor further comprising a second light emitting element that is provided in the first surface side of the transparent body for emitting the light toward the transparent body, wherein:

the light guide body includes:
a first light passage that guides the light, which is emitted by the first light emitting element, to the transparent body and guides the reflected light, which is reflected by the transparent body, toward the light receiving element; and
a second light passage that guides the light, which is emitted by the second light emitting element, to the transparent body and guides the reflected light, which is reflected by the transparent body, toward the light receiving element;
the first light emitting element is provided apart from the light receiving elements by a first distance;
the second light emitting element is provided apart from the light receiving elements by a second distance, which is different from the first distance; and
the light guide body further includes a converging portion that converges the light, which travels through the first light passage, to the light receiving element, and converges the light, which travels through the second light passage, to the light receiving element.

6. The raindrop sensor according to claim 2, wherein:
the light guide body includes a prism portion and a silicone portion, which is held between an end surface of the prism portion and the first surface of the transparent body;
the light, which travels through the first light passage, is reflected by the second surface of the transparent body, and the reflected light is guided toward the first light receiving element through the first light passage;
the light, which travels through the second light passage, is reflected by the second surface of the transparent body, and the reflected light is guided toward the second light receiving element through the second light passage; and
the light guide body further includes a third light passage that guides the light, which is emitted by the light emitting element, to the end surface of the prism portion and guides the reflected light, which is reflected by the end surface of the prism portion, toward the first light receiving element.

7. The raindrop sensor according to claim 4, wherein:
the light guide body includes a prism portion and a silicone portion, which is held between an end surface of the prism portion and the first surface of the transparent body;
the light, which is emitted by the first light emitting element and travels through the first light passage, is reflected by the second surface of the transparent body, the reflected light being guided toward the fist light receiving element through the first light passage;
the light, which is emitted by the second light emitting element and travels through the second light passage, is reflected by the second surface of the transparent body, the reflected light being guided toward the second light receiving element through the second light passage; and
the light guide body includes a third light passage that guides the light emitted by the second light emitting element to the end surface of the prism portion and guides the reflected light, which is reflected by the end surface of the prism portion, toward the first light receiving element.

8. The raindrop sensor according to claim 5, wherein:
the light guide body includes a prism portion and a silicone portion, which is held between an end surface of the prism portion and the first surface of the transparent body;
the light, which is emitted by the first light emitting element and travels through the first light passage, is reflected by the second surface of the transparent body, the reflected light being guided toward the light receiving element through the first light passage;
the light, which is emitted by the second light emitting element and travels through the second light passage, is reflected by the second surface of the transparent body, the reflected light being guided toward the light receiving element through the second light passage; and
the light guide body includes a third light passage that guides the light, which is emitted by the first light emitting element, to the end surface of the prism portion and guides the reflected light, which is reflected by the end surface of the prism portion, toward the light receiving element.

* * * * *